United States Patent [19]

Backhouse

[11] Patent Number: 4,751,311

[45] Date of Patent: Jun. 14, 1988

[54] ISOTHIAZOLONE AQUEOUS SOLUTIONS

[75] Inventor: Bryan S. Backhouse, Sowerby Bridge, England

[73] Assignee: Imperial Chemical Industries, Hertfordshire, England

[21] Appl. No.: 881,780

[22] Filed: Jul. 3, 1986

[30] Foreign Application Priority Data

Jul. 10, 1985 [GB] United Kingdom ............... 8517478

[51] Int. Cl.$^4$ .................... A01N 43/80; C07D 275/04
[52] U.S. Cl. .................................. 548/209; 548/213
[58] Field of Search .................. 548/209, 213; 564/3, 564/32; 514/372, 373

[56] References Cited

U.S. PATENT DOCUMENTS 3,870,795  3/1975  Miller et al. ..................... 548/213
4,661,503  4/1987  Martin et al. ..................... 514/372

FOREIGN PATENT DOCUMENTS 0765108  9/1971  Belgium ............................ 514/373
884541   12/1961  United Kingdom .

OTHER PUBLICATIONS

Krzeminski, et al., Journal of Agricultural Food Chemistry, vol. 23, No. 6, pp. 1069–1075.
European Search Report.

*Primary Examiner*—Donald G. Daus
*Assistant Examiner*—Diana G. Rivers
*Attorney, Agent, or Firm*—Cushman, Darby & Cushman

[57] ABSTRACT

Concentrated aqueous formulations of isothiazolin-3-ones containing 5–30% urea are stable down to −13 deg C. at pH>9.

3 Claims, No Drawings

ISOTHIAZOLONE AQUEOUS SOLUTIONS

This invention relates to new biocidal compositions and more particularly to aqueous solutions of isothiazolones.

Many isothiazolin-3-ones are known to be effective agent as biocides. In various type of applications, it is necessary or convenient to formulate the isothiazolin-3-ones in solution, especially in water or organic solvents. For example 1,2-benzisothiazolin-3-one solutions are used for the protection of aqueous media against infection by microorganisms.

Other application include fungicidal seed treatment, uses as preservatives for cutting oils or paints or in water-cooling systems, sanitizing additives for soaps and detergents, bacteriostats and mildewstats for paper products or leather, wood surfaces or fabrics.

1,2 benzoisothiazolin-3-one (sometimes herein referred to as BIT) is obtained in a unpurified form which is however entirely satisfactory for most purposes and is used in the form of an aqueous dispersion or paste. Such dispersions or pastes are cost effective but suffer from the disadvantage that they tend to settle out on standing, contain dispersed impurities, and may have variable physical properties.

Isothiazolin-3-ones unsubstituted on the nitrogen atom are known to form salts with alkali metals, for example sodium and potassium, and with ammonia or amines such as triethanolamine. These salts are generally water-soluble.

U.K. Pat. No. 1,191,253 describes and claims high strength aqueous solutions of crude 1,2-benzoisothiazolin-3-one in the form of a mixture of two or more different amine salts thereof, the amines being selected from diethanolamine, triethanolamine, diisopropanol amine, triisopropanolamine and morpholine.

U.K. Pat. No. 1,330,531 discloses compositions of 1,2-benzisothiazolin-3-one in aliphatic, cycloaliphatic or heterocyclic amines which contain 2 to 6 carbon atoms and which are free from hydroxyl and ether groups.

U.S. Pat. No. 2,004,747 discloses solution of alkali metal salt of 1,2-benzisothiazolin-3-one in a hydroxylic organic solvent such as propylene glycol, dipropylene glycol and polyethylene glycols.

However such salt solutions require the addition of considerable quantities of extra organic solvent, for example glycols, to be stable enough to be commercially acceptable. The addition of organic solvents such as propylene glycol is expensive.

It was therefore still desirable to provide isothiazolin-3-ones, more particularly 1,2-benzisothiazolin-3-one, in strong, low-temperature stable aqueous solution using cheaper and readily available compatible stabilisers or antifreeze agents.

According to the present invention, there are provided basic aqueous solutions comprising a N-unsubstituted isothiazolone of the formula $$\begin{array}{c} R_1 \diagdown C \diagup \overset{O}{\underset{\|}{C}} \diagdown \\ \phantom{R_1 \diagdown} \| \phantom{C} NH \\ R_2 \diagup C \diagdown S \diagup \end{array}$$

wherein R1 and R2 are independently hydrogen, benzyl, C1–C4 alkyl, aryl, halogen, or taken together complete a monounsaturated cyclo-alkyl ring or a benzene ring, optionally substituted with one or more halogen atoms, nitro groups or C1–C4 alkyl or alkoxy groups, and up to 40% by weight of urea.

A preferred compound is the one wherein R1 and R2 together complete an unsubstituted benzene ring. Other preferred compounds include derivatives wherein R1 and R2 are each methyl or, together, form a cyclopentene ring.

Urea acts as an effective antifreeze additive and the above aqueous solutions are storage stable for several weeks.

Using Differential Scanning Calorimetry (DSC) methods, in the case of 10% aqueous 1,2-benzoisothiazolin-3-one it has been demonstrated that the latter forms with urea a ternary eutectic composition at a temperature of about −13 deg C. and a concentration of 28% urea.

Consequently, the preferred concentration of urea in a 10% BIT/NaOH solution is ranging from 18 to 30% urea, preferably about 25% by weight.

A preferred base to maintain the pH above 9 is an alkali metal hydroxide, for example sodium hydroxide. A moderate excess of such base used to form a isothiazolin-3-one salt is not detrimental to the stability of the solutions of isothiazolin-3-ones.

In contrast to other commercially available formulations of isothiazolin-3-ones, it has also been observed that the solutions according to the present invention may be further diluted with water providing again stable aqueous solutions. This feature is of considerable advantage and provides flexibility of use of such BIT formulations. It is indeed desirable to provide a concentrated stock solution that may be subsequently diluted for particular purposes.

It has been demonstrated furthermore that the presence of urea has no adverse effect on the antimicrobial properties of the formulations in accordance with the invention.

For example, the minimum inhibitory concentration (MIC) of 1,2-benzisothiazolin-3-one in nutrient broth is not changed when compared to other commercial formulations.

Thus most biocide applications of isothiazolin-3-ones are retained and, urea being generally recognized as a safe additive in the food industry, the above formulations may be used in indirect food contact applications, for example adhesives for packaging. Other applications include in-can preservation of water-based paints.

Most other ingredients used as stabilisers of isothiazolin-3-one solutions may also be added to the formulations in accordance with the invention.

EXAMPLES

1. Method of Preparation

Commercial grade 1,2 benzoisothiazolin-3-one (BIT) aqueous paste was weighed into a 600 ml beaker to give 9,25% w/w on final formulation. Tap water was added and the slurry agitated with a mechanical stirrer, while being heated by a water bath at 70 deg C. Sufficient NaOH solution was added to ensure that the BIT was in the sodium salt form (i.e. pH 9.5 approx.). 8 w/w of 10N NaOH solution was required. Addition was completed in ½ h and during the addition the BIT dissolved. When the pH stabilised at 9.5 the solution was cooled to 45 degrees C. in the water bath and the required level of urea was added (causing further cooling as it dissolved).

The solution containing urea was filtered through a 12.5 cm 'Whatman' (trademark) 54 paper using partial vacuum on a Buchner funnel. Replacing sodium hydroxide by other bases such as LiOH, KOH, NH4OH, ethylene diamine, diethanolamine, a similar procedure was used to provide the corresponding solutions at pH 9.5.

2. Stability of the Urea Formulations to Further Dilution with Water

A 9.25% BIT solution using sodium hydroxide as base and containing 30% urea, was diluted to 3% BIT active agent content at ambient temperature with tap water. The following commercial formulations of BIT were also diluted to 3% BIT active agent content under similar conditions.
(1) A 10% formulation of sodium BIT in aqueous propylene glycol/sodium hydroxide.
(2) A 20% formulation of sodium BIT in aqueous dipropylene glycol/sodium hydroxide
(3) A 33% formulation of the ethylene diamine salt of BIT in excess aqueous ethylene diamine.

The dilute solution prepared from the three commercial solvent formulations precipitated in less than 24 hours. The dilute solution prepared from the urea formulation was stable for at least 4 weeks.

3. Biocidal Activity of Urea Formulation of BIT

Minimum Inhibitory Concentration (MIC) of BIT in nutrient broth (24 hours/37 deg C.)

|  | MIC ppm as product | | | | |
|---|---|---|---|---|---|
|  | S. aureus | E. coli | P. aeruginosa | P. vulgaris | P. cloacae |
| Commercial formulation of 10% BIT sodium salt in propylene glycol/NaOH | 1000 | 1000 | 1000 | 1000 | 250 |
| 10% BIT sodium salt in 30% aqueous urea | 1000 | 1000 | 1000 | 1000 | 250 |

What is claimed is:

1. An aqueous solution wherein the isothiazolin-3-one is present at a concentration of about 10% by weight and the urea at a concentration ranging from 18 to 30% by weight.

2. A basic aqueous solution comprising 1,2-benzisothiazolin-3-one and up to 40% by weight urea based on the weight of the solution.

3. The solution of claim 2 wherein the 1,2-benzisothiazolin-3-one is present in an amount up to 10% by weight based on the weight of the solution.

* * * * *